United States Patent
Machida et al.

(10) Patent No.: US 6,585,938 B1
(45) Date of Patent: Jul. 1, 2003

(54) GAS CONCENTRATION-DETECTING DEVICE FOR DETECTING CONCENTRATION OF GAS IN OIL

(75) Inventors: Kyoichi Machida, Saitama-ken (JP); Nobuyuki Ohta, Saitama-ken (JP); Katsunori Makino, Saitama-ken (JP); Hayao Karasaki, Tokyo (JP)

(73) Assignee: Honda Giken Gokyo Kabushiki Kaisha, Tokyo (JP)

( * ) Notice: Subject to any disclaimer, the term of this patent is extended or adjusted under 35 U.S.C. 154(b) by 18 days.

(21) Appl. No.: 09/630,120

(22) Filed: Aug. 1, 2000

(30) Foreign Application Priority Data

Aug. 3, 1999  (JP) .......................................... 11-220210

(51) Int. Cl.⁷ .............................................. G01N 27/00
(52) U.S. Cl. .......................... 422/98; 422/68.1; 422/80; 422/83; 436/60; 436/149
(58) Field of Search ............................ 422/98, 68.1, 80, 422/83; 204/424, 425, 432, 415; 73/19.02, 19.01, 19.11, 53.05, 25.01; 250/343; 324/425; 436/60, 149

(56) References Cited

U.S. PATENT DOCUMENTS

| | | | | |
|---|---|---|---|---|
| 4,444,040 A | * | 4/1984 | Sakai et al. ................. | 73/19.02 |
| 4,571,543 A | * | 2/1986 | Raymond et al. ............ | 324/425 |
| 4,763,514 A | * | 8/1988 | Naito et al. ................ | 73/19.11 |
| 5,062,292 A | * | 11/1991 | Kanba et al. ............... | 73/19.01 |
| 5,269,175 A | * | 12/1993 | Chmiel et al. .............. | 73/53.05 |
| 5,522,980 A | * | 6/1996 | Hobbs et al. ................ | 204/432 |
| 5,804,703 A | * | 9/1998 | Wind et al. ................. | 73/25.01 |
| 5,993,624 A | * | 11/1999 | Matsubara et al. ......... | 204/424 |
| 6,037,592 A | * | 3/2000 | Sunshine et al. ............ | 250/343 |
| 6,165,336 A | * | 12/2000 | Maki et al. .................. | 204/415 |
| 6,287,439 B1 | * | 9/2001 | Kato et al. ................... | 204/425 |

* cited by examiner

*Primary Examiner*—Jill Warden
*Assistant Examiner*—Brian Sines
(74) *Attorney, Agent, or Firm*—Lahive & Cockfield, LLP (57) ABSTRACT

There is provided a gas concentration-detecting device for detecting the concentration of gas in oil, which is capable of detecting the concentration of gas in oil with accuracy, irrespective of the temperature of oil, and even when oil is degraded. The gas concentration-detecting device includes two electrodes for being arranged in the oil such that the electrodes are opposed to each other and spaced from each other by a predetermined distance, and a capacitance amplifier for outputting a signal indicative of a concentration of gas in oil, the signal being dependent on a capacitance between the electrodes. The predetermined distance between the electrodes is set to a value equal to or larger than a predetermined value at which an amount of drift of the signal output from the capacitance amplifier dependent on variation in a temperature of the oil starts to gradually decrease as the distance between the electrodes is increased.

24 Claims, 9 Drawing Sheets

GAS CONCENTRATION-DETECTING DEVICE FOR DETECTING CONCENTRATION OF GAS IN OIL

BACKGROUND OF THE INVENTION

1. Field of the Invention

This invention relates to a gas concentration-detecting device for detecting the concentration of gas, such as air or the like, in oil by detecting a capacitance (electrostatic capacitance) between a plurality of electrodes arranged in the oil.

2. Description of the Prior Art

Generally, in a lubricating system of an industrial machine, when the concentration of gas, such as air or the like, in oil increases, the lubricating performance of the oil decreases to cause metal contact or the like, and in the worst case, seizure of sliding portions and rotating portions is brought about. Further, in an actuating system of the industrial machine as well, if the concentration of gas in oil increases, there is a fear that hydraulic pressure decreases to make an actuating member of the system inoperative or cause a delay in response or an erroneous operation of the member. To prevent such inconveniences, it is desirable to periodically detect and check the concentration of gas in oil. Conventionally, as gas concentration-detecting devices for detecting the concentration of gas in oil, there have been proposed (1) one for calculating the concentration of gas by sampling a predetermined amount of oil from a lubricating system or an actuating system of a machine, and determining a volume ratio of gas contained in the oil, (2) one for providing a bypass passageway bypassing an oil path and having a volumeter or a weightometer arranged therein, and calculating back the concentration of gas based on a density per volume of the oil determined by using the volumeter or the weightometer, and (3) one for detecting the concentration of gas by arranging a capacitance sensor comprised of two electrodes in oil and detecting a capacitance between the two electrodes.

The above conventional gas concentration-detecting device (1) is constructed such that sampling of the oil is necessary as described above. However, it is impossible to carry out sampling operations in a manner coping with changes in the gas concentration, so that transient changes in the gas concentration cannot be detected in real time. Therefore, when the gas concentration-detecting device is applied to a lubricating system or an actuating system, if the gas concentration sharply increases in a short time period, the device cannot detect the change, which sometimes causes the above-mentioned inconveniences. Further, the amount of oil is changed by sampling thereof, causing a change in the state of a mixture of gas and oil, which can increase an error in the detection of a gas concentration. Further, in the gas concentration-detecting device (2), oil is caused to flow through the bypass passageway. The concentration of gas in oil present within the passageway is sometimes different from an actual concentration of gas in oil present in the oil path. In such a case as well, an error in the detection of a gas concentration is increased. Furthermore, the provision of the bypass passageway and the volumeter or weightometer results in an increased size of the system and increased manufacturing costs of the industrial machine.

On the other hand, the gas concentration-detecting device (3) is generally constructed such that a relatively small-sized capacitance sensor is directly inserted into or mounted in an oil path. Further, the output from the capacitance sensor is highly responsive to changes in the gas concentration, so that it is possible to detect transient changes in the gas concentration in real time. Therefore, the gas concentration-detecting device (3) is free from the inconveniences with the above gas concentration-detecting devices (1) and (2). In the device (3), however, the output from the capacitance sensor is susceptible to a change in oil temperature and varies with this change. Further in a region of the oil temperature beyond a predetermined value, the higher the oil temperature becomes, the more significant drift of the sensor output is caused (in this specification, the term "drift" of an output from a capacitance sensor is used to mean deviation of an actual value of the output from the capacitance sensor obtained when the capacitance sensor is placed e.g. in 100% oil having no gas mixed therein, from an assumed value of the output from the capacitance sensor which the capacitance sensor is to output assuming that the output from the sensor placed in the 100% oil varies with a predetermined difference from an output from the sensor placed in 100% gas). Therefore, when the output from the capacitance sensor suffers from a significant drift as described above, gas concentration detection accuracy of the device is lowered. Further, when the oil is degraded as well, the output from the capacitance sensor suffers from a drift, resulting in a lowered gas concentration detection accuracy of the device.

SUMMARY OF THE INVENTION

It is an object of the invention to provide a gas concentration-detecting device which is capable of detecting the concentration of gas in oil with accuracy, irrespective of the temperature of oil, and even when the oil is degraded.

To attain the above object, the present invention provides a gas concentration-detecting device for detecting a concentration of gas in oil, comprising:

a plurality of electrodes for being arranged in the oil such that the electrodes are opposed to each other and spaced from each other by a predetermined distance; and gas concentration detection means for outputting a signal indicative of the concentration of the gas in the oil, the signal being dependent on a capacitance between the electrodes, wherein the predetermined distance between the electrodes is set to a value equal to or larger than a predetermined value at which an amount of drift of the signal output from the gas concentration detection means dependent on variation in a temperature of the oil starts to gradually decrease as a distance between the electrodes is increased.

According to this gas concentration-detecting device for detecting a concentration of gas in oil, the gas concentration detection means outputs a signal indicative of a detected concentration of gas in oil and dependent on a capacitance between the plurality of electrodes. Hence, it is possible to detect the concentration of the gas in real time, while coping with the change in the concentration of the gas. Generally, a signal indicative of a capacitance between two electrodes in oil varies with the temperature of the oil, and an amount of drift occurring at the time is reduced as the distance between the two electrodes is increased. More specifically, as the distance between the two electrodes is decreased, the amount of drift has a characteristic that it sharply decreases before the distance becomes equal to a predetermined value, and gradually decreases as the distance is increased beyond the predetermined value. In the present invention, attention is paid to the above characteristic of the amount of drift, and the predetermined distance between the two electrodes is set to a value equal to or larger than the predetermined value at which the amount of drift of the signal output from the gas concentration detection means dependent on variation in the temperature of the oil starts to gradually decrease as the distance between the electrodes is increased. This makes it possible to effectively minimize the amount of drift of the signal, and thereby detect the concentration of gas in oil with accuracy irrespective of the temperature of oil.

Preferably, the gas concentration-detecting device further includes oil temperature detection means for detecting the temperature of the oil, and correction means for correcting the signal output from the gas concentration detection means, according to the temperature of the oil detected by the oil temperature detection means.

According to this preferred embodiment, by using the correction means, the signal output from the gas concentration detection means containing the above amount of drift can be corrected, according to the temperature of the oil detected by the oil temperature detection means. This makes it possible to compensate for the influence of a change in the temperature of the oil on the signal, thereby enhancing the accuracy of detection of the gas concentration.

More preferably, the predetermined distance between the electrodes is set to a value within a range between the predetermined value and a second predetermined value which is larger than the predetermined value, the range being determined based on a characteristic of the amount of drift of the signal output in relation to degradation of the oil.

Generally, the signal indicative of a capacitance between two electrodes in oil has a characteristic that it is drifted by degradation of oil, and the amount of the drift simply increases as the distance between the two electrodes is increased, so long as the distance electrodes is equal to or larger than a certain value. In this preferred embodiment, attention is paid to the above characteristic of the amount of drift, and the predetermined distance between the electrodes is set to a value within a range between the predetermined value and a second predetermined value which is larger than the predetermined value, the range being determined based on the characteristic of the amount of drift of the signal in relation to degradation of the oil. Therefore, if the second predetermined value is set to a value which can sufficiently minimize the amount of drift caused by degradation of oil, it is possible to suppress not only a drift of the signal output from the gas concentration detection means due to a change in oil temperature, but also a drift of the same due to degradation of oil. This makes it possible to detect the concentration of gas in the oil with higher accuracy.

Preferably, the gas concentration detection means comprises a capacitance amplifier which applies a predetermined voltage to the electrodes and detects a voltage generated in response to the application of the predetermined voltage, dependent on the capacitance between the electrodes to output the voltage as the signal.

More preferably, the correction means includes a lookup table formed by correlating actual measurement values of two kinds of the voltage output from the capacitance amplifier in respective cases of application of the predetermined voltage carried out when the concentration of the gas in the oil is 100% and when the concentration of the gas in the oil is 0% to corresponding values of the temperature of the oil assumed when the application of the predetermined voltage is carried out, and interpolation calculation means for carrying out interpolation calculation by using two values of the actual measurement values of the respective two kinds read from the lookup table according to the temperature of the oil detected by the oil temperature detection means, and an actual value of the voltage output from the capacitance amplifier.

The above and other objects, features, and advantages of the invention will become more apparent from the following detailed description taken in conjunction with the accompanying drawings.

DETAILED DESCRIPTION

The invention will now be described in detail with reference to the drawings showing embodiments thereof. In the embodiments, a gas concentration-detecting device for detecting the concentration of gas in oil according to the invention is applied to a lubricating system, not shown, of an automotive engine, not shown.

Figure 1:
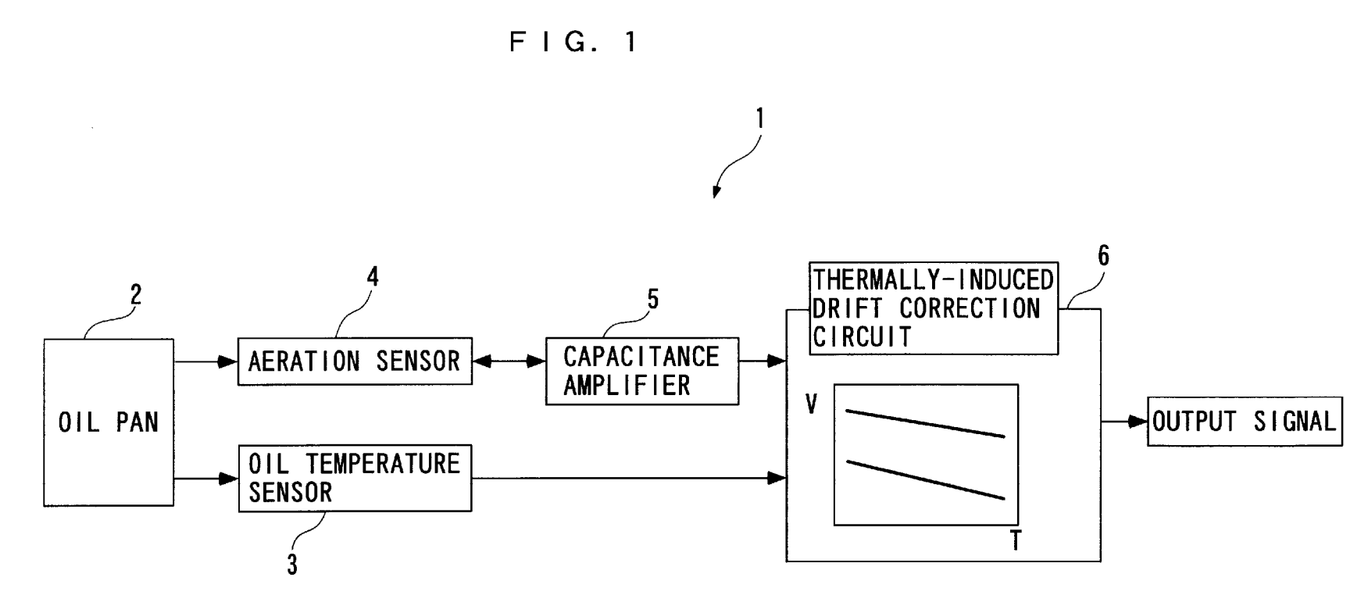
FIG. 1 is a block diagram schematically showing the arrangement of a gas concentration-detecting device for detecting the concentration of gas in oil, according to a first embodiment of the invention.

Referring to FIG. 1, there is schematically shown the arrangement of the gas concentration-detecting device 1, which is used for detecting the concentration of air 8 (see FIG. 3) i.e. gas contained in oil 7 (see FIG. 3) in an oil pan 2 for the automotive engine. The oil pan 2 has an oil temperature sensor 3 (oil temperature detection means) and an aeration sensor 4 mounted therein. The oil temperature sensor 3 is arranged on a bottom wall of the oil pan 2 such that it protrudes into the inside of the oil pan 2 (not illustrated in the drawings). The oil temperature sensor 3 is formed by a thermistor and detects a temperature T of the oil 7 to output a signal indicative of the detected temperature T.

Figure 2A:
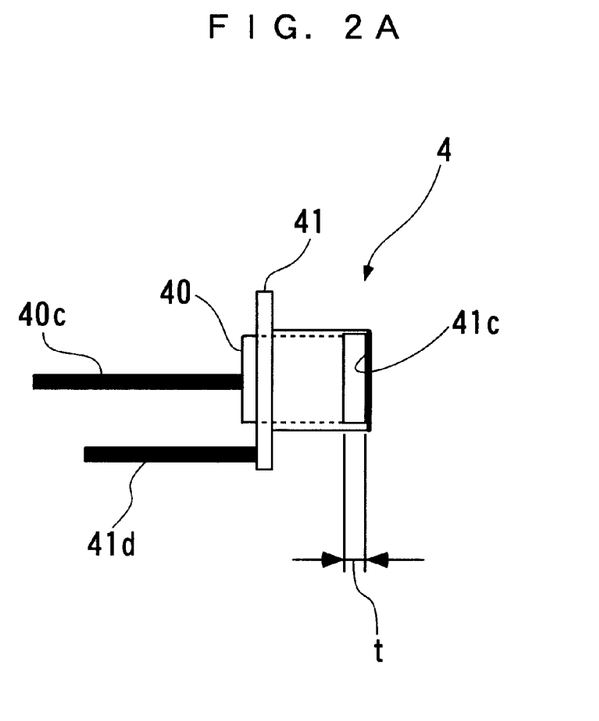
FIG. 2A is a side view schematically showing the arrangement of an aeration sensor of the gas concentration-detecting device.
Figure 2B:
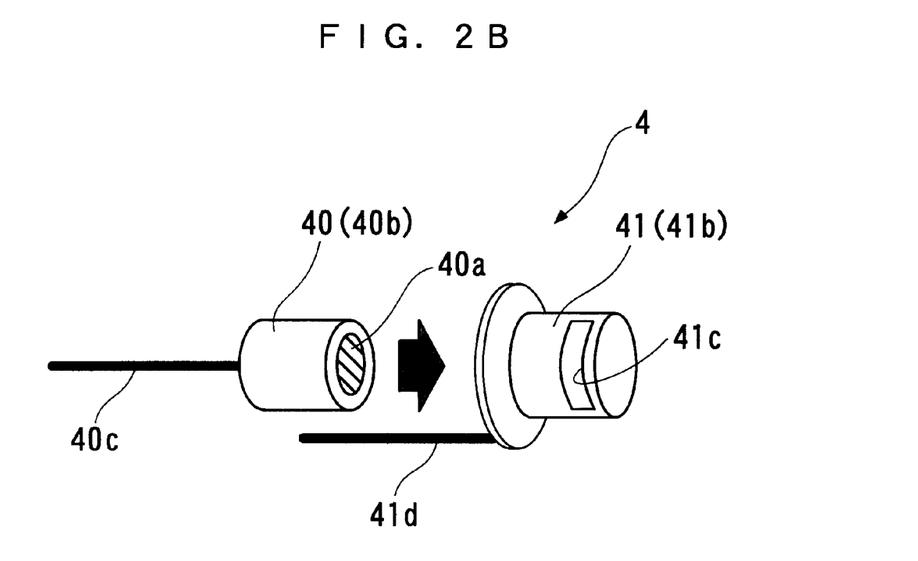
FIG. 2B is an exploded perspective view showing the arrangement of the aeration sensor of the gas concentration-detecting device.

Similarly to the oil temperature sensor 3, the aeration sensor 4 is arranged on the bottom wall of the oil pan 2 such that it protrudes into the inside of the oil pan 2 (not illustrated in the drawings). The aeration sensor 4 is used to detect the concentration AC of the air 8 (concentration of gas) in the oil 7 by cooperation of the same and a capacitance amplifier 5 (gas concentration detection means), referred to hereinafter. As shown in FIGS. 2A and 2B, the aeration sensor 4 is composed by a combination of two inner and outer electrode portions 40, 41. The inner electrode portion 40 includes a disk-shaped electrode 40a, and a casing 40b having a hollow cylindrical shape with open opposite ends and having the electrode 40a fitted therein. The electrode 40a is formed e.g. of a coated copper alloy plate (or a stainless plate) having an area S, and arranged at one end of the casing 40b such that the electrode 40a is flush with the one end of the casing 40b. The casing 40b is formed of an electrically non-conductive material, such as a synthetic resin or the like. Further, the electrode 40a has a lead wire 40c electrically connected thereto, and the lead wire 40c extends further from the other end of the casing 40b.

Figure 3:
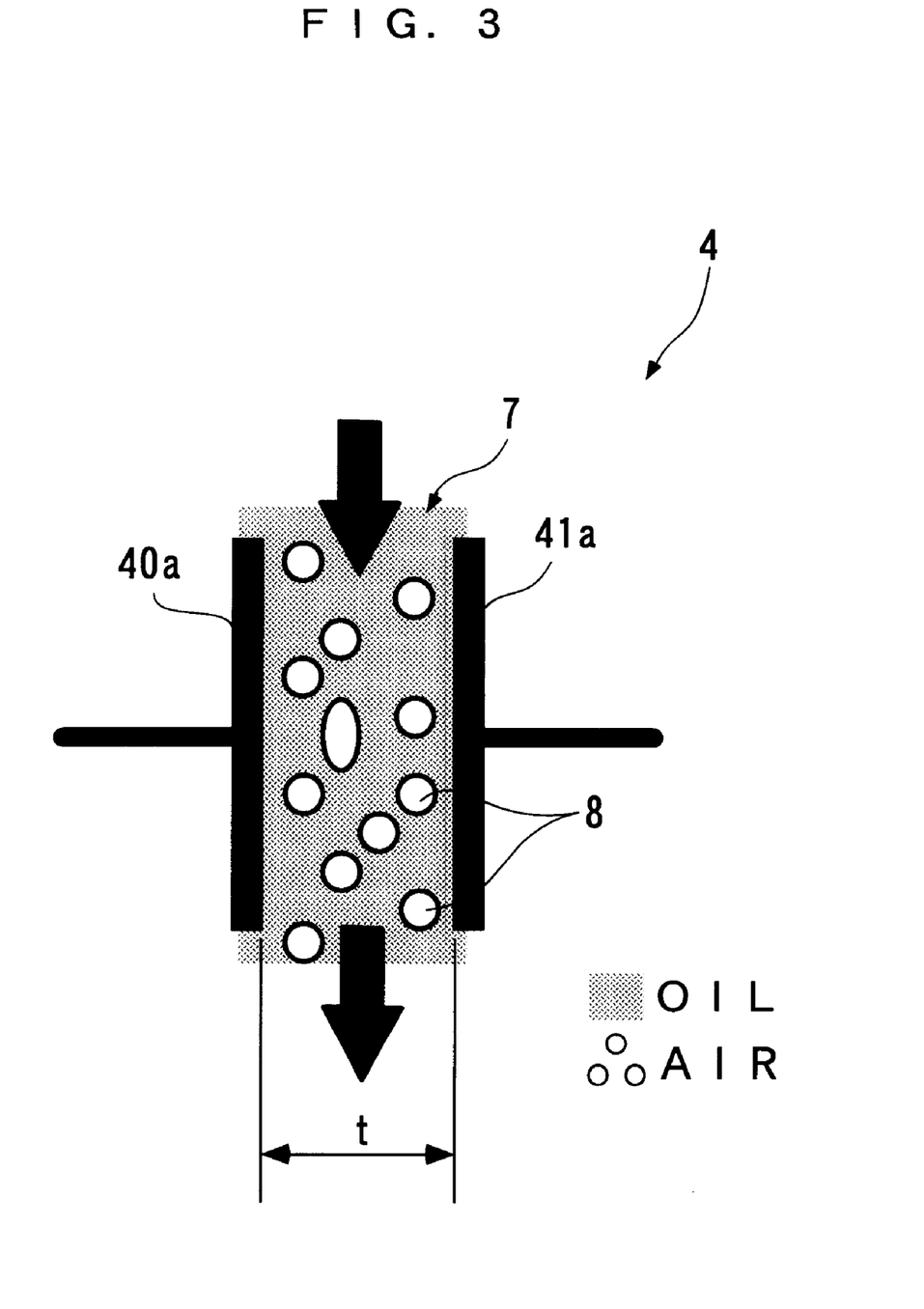
FIG. 3 is a diagram which is useful in explaining an operation of the aeration sensor shown in FIGS. 2A and 2B.

The outer electrode potion 41 includes an electrode 41a (see FIG. 3) formed e.g. of a coated copper alloy plate (or a stainless plate), and a casing 41b having a hollow cylindrical shape. The casing 41b is formed of stainless steel, for instance, and has one open end and the other bottomed end closed by a bottom wall. The inner electrode portion 40 is mounted in the outer electrode potion 41 such that the casing 40b of the inner electrode portion 40 is fitted in an inner hole of the casing 41b from the open end of the casing 41b. The electrode 41a is arranged on an inner surface of the bottom wall of the casing 41b in a manner opposed to the electrode 40a of the inner electrode portion 40, and has the same area S as that of the electrode 40a. Further, the casing 41b has a side wall formed with a slit 41c which extends circumferentially and through the side wall at a location corresponding to the electrodes 40a, 41a. This slit 41c has a width equal to a distance t (hereinafter referred to as the "interelectrode distance t") between the electrodes 40a, 41a. In the present embodiment, the interelectrode distance t is set to 3 mm (a predetermined distance) for a reason described hereinbelow. As shown in FIG. 3, the oil 7 in the oil pan 2 flows into the aeration sensor 4 via the slit 41c, and fills space between the electrodes 40a, 41a. Further, the electrode 41a has a lead wire 41d electrically connected thereto, and the lead wire 41d extends further from a flange of the open end of the casing 41b.

The lead wires 40c, 41d are also connected to the capacitance amplifier 5. The capacitance amplifier 5 in operation applies an alternating current voltage having a predetermined frequency (e.g. of 100 Hz to 50 kHz) to the aeration sensor 4, and detects a voltage dependent on a capacitance C between the electrodes 40a, 41a occurring during the application of the alternating current voltage to output a signal indicative of the detected voltage. The signal or output V from the capacitance amplifier 5 is a voltage signal indicative of the capacitance C by its voltage value (unit: V).

The capacitance amplifier 5 and the oil temperature sensor 3 are connected to a thermally-induced drift correction circuit 6 (correction means), and the output V indicative of the capacitance C and a signal indicative of a detected oil temperature are input to the thermally-induced drift correction circuit 6, from the capacitance amplifier 5 and the oil temperature sensor 3, respectively. The thermally-induced drift correction circuit 6 calculates a concentration AC (%) of air contained in the oil 7, based on the oil temperature T and the output V from the capacitance amplifier 5 by a calculation method, described hereinafter, and further delivers an output signal indicative of the calculated concentration AC of air in the oil (hereinafter referred to as "the air concentration AC").

Next, the relationship between the capacitance C between the electrodes 40a, 41a and the air concentration AC of the air 8 in the oil 7 will be briefly described. Generally, the capacitance C between the two electrodes 40a, 41a is determined based on an electrode area S of each electrode, an interelectrode distance t, a vacuum dielectric constant $\in_0$, and an interelectrode dielectric constant $\in$, by using the following equation (1):

$$C = (S/t) \cdot \in_0 \cdot \in \qquad (1)$$

In the above equation (1), the vacuum dielectric constant $\in_0$ is a constant, and the electrode area S and the interelectrode distance t are fixed values which are set when the aeration sensor 4 is manufactured. Therefore, the capacitance C is proportional to the interelectrode dielectric constant $\in$. Further, the interelectrode dielectric constant $\in$ is a dielectric constant of the oil 7 present between the electrodes 40a, 41a and having the air 8 mixed therein, which varies with the air concentration AC of the oil 7. Therefore, the capacitance C proportional to the interelectrode dielectric constant $\in$ changes according to the change in the air concentration AC of the oil 7. By detecting the capacitance C with the aeration sensor 4 based on the above-mentioned relationship between the capacitance C and the air concentration AC of the oil 7, it is possible to detect the air concentration AC of the oil 7. The method of detecting the air concentration AC will be described in further detail hereinafter.

Figure 4:
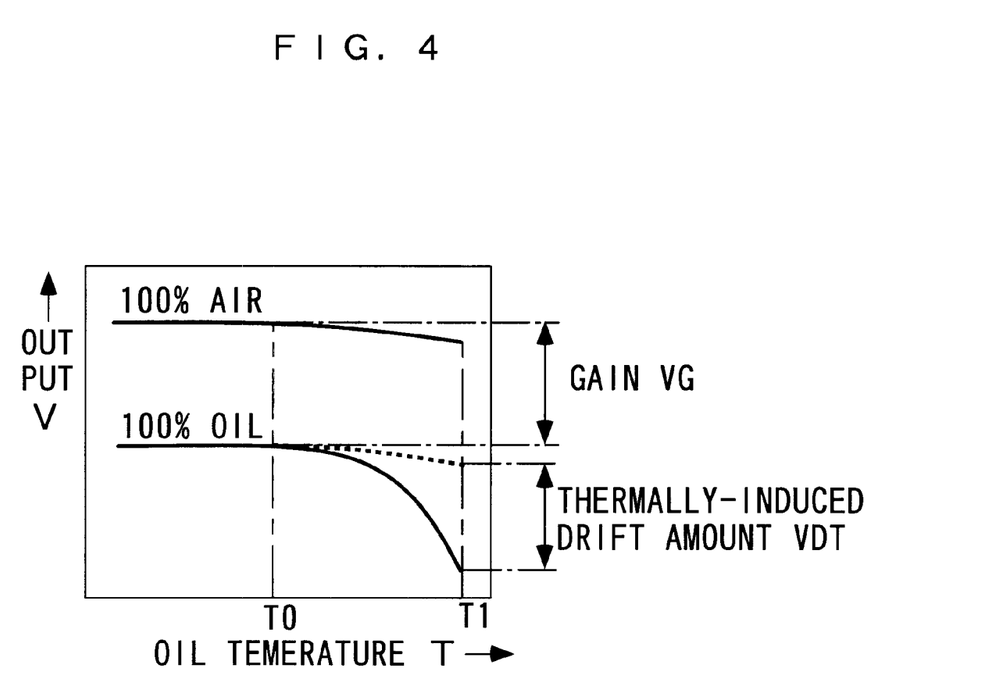
FIG. 4 is a diagram showing the relationship between an oil temperature T and an output V from a capacitance amplifier.

Now, the aforementioned reason that the interelectrode distance t in the aeration sensor 4 is determined to be 3 mm will be described with reference to graphs of FIGS. 4 to 8. First, FIG. 4 shows an example of results of measurements of the output V from the capacitance amplifier 5 of the gas concentration-detecting device 1. In this example, the output V from the capacitance amplifier 5 is measured by using the aeration sensor 4 having the predetermined electrode area S and the predetermined interelectrode distance t, while varying the oil temperature T. In FIG. 4, an upper solid line in the graph shows data obtained by measuring the output V from the capacitance amplifier 5 when only the air 8 exists between the electrodes 40a, 41a (this state is denoted as "100% AIR" in the graph. The same applies to other graphs referred to hereinafter). A lower solid line in the graph shows data obtained by measuring the output V from the capacitance amplifier 5 when only the oil 7 exists between the electrodes 40a, 41a (this state is denoted as "100% OIL" in the graph. The same applies to other graphs referred to hereinafter).

As shown in FIG. 4, for an identical oil temperature T, the difference (hereinafter referred to as the "gain VG") in the output V between measurement data in the case of 100% air and measurement data in the case of 100% oil is characterized in that the gain VG is approximately fixed when the oil temperature T is equal to or lower than a value T0 (e.g. within 80 to 100° C.), whereas when the oil temperature T becomes higher than the value T0, the gain VG increases. The value of the oil temperature T changes according to the physical properties of the oil 7 and the frequency of voltage applied by the capacitance amplifier 5.

A dotted line in the graph shows an output V from the capacitance amplifier 5 in the case of 100% oil, assuming that the gain VG relative to the output from the capacitance amplifier 5 in the case of 100% air is fixed (equal to a value assumed when the oil temperature T is equal to or lower than the value T0) irrespective of the oil temperature T. Hereinafter, data of the above output V shown by the dotted line is referred to as the "reference data". Comparison between the reference data indicated by the dotted line and the measurement data of the output in the case of 100% oil shown by the lower solid line shows that the difference therebetween tends to increase as the oil temperature T becomes higher beyond the value T0. Hereinafter, the absolute value of the difference in the output V between the measurement data in the case of 100% oil and the reference data, both of which are obtained when the oil temperature T is equal to a predetermined value T1, is referred to as the "thermally-induced drift amount VDT" (amount of drift). The predetermined value T1 is set to a certain high temperature (e.g. 130° C.) as a reference value used in defining the thermally-induced drift amount VDT. Generally, it is preferred that the output V from the capacitance amplifier 5 varies as linearly as possible with respect to changes in the oil temperature T from the viewpoint of detection accuracy, and hence it is preferable to make the thermally-induced drift amount VDT as small as possible. It should be noted that although the difference between the measurement data in the case of 100% oil and the reference data sometimes assumes a negative value, depending on the circuit configuration of the capacitance amplifier 5, in such a case as well, it is only required that the absolute value of the difference is set to the thermally-induced drift amount VDT.

Figure 5A:
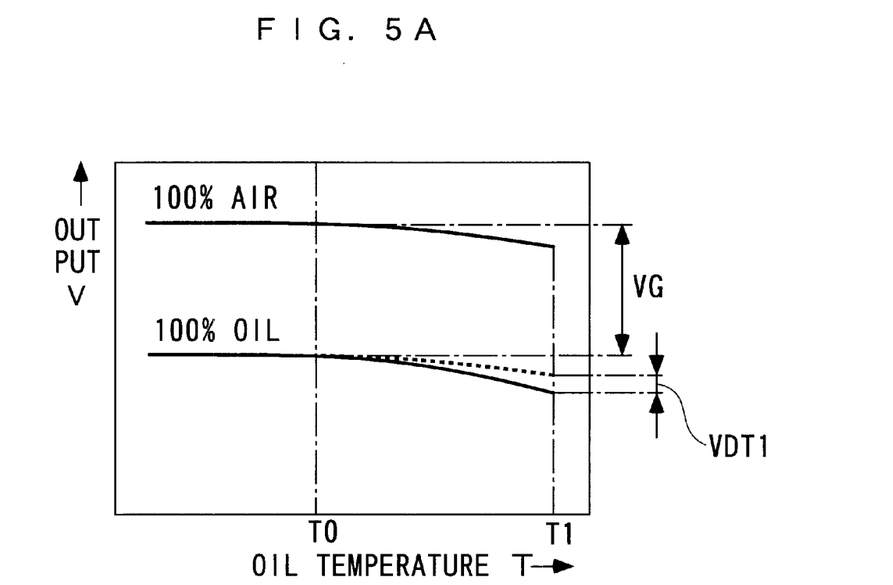
FIG. 5A is a diagram showing the relationship between the oil temperature T and the output V from the capacitance amplifier, which is useful in explaining a case of a thermally-induced drift being small.
Figure 5B:
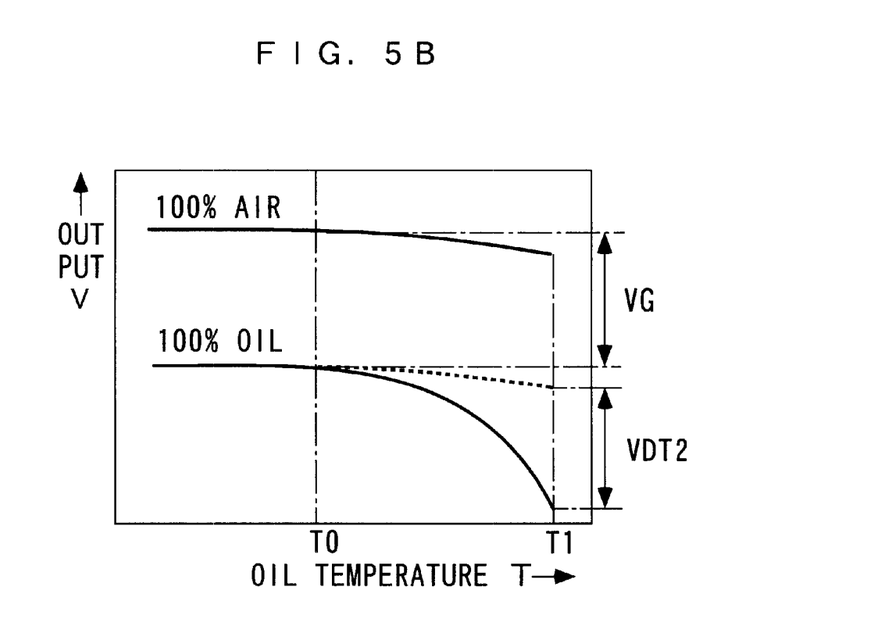
FIG. 5B is a diagram showing the relationship between the oil temperature T and the output V from the capacitance amplifier, which is useful in explaining a case of the thermally-induced drift being large.

FIGS. 5A and 5B show examples of results of measurements of the output V from the capacitance amplifier 5 carried out by using first and second aeration sensors 4, respectively, adjusting the amplification factor of the capacitance amplifier 5 such that the same gain VG is obtained for the two sensors when the oil temperature T is equal to the value T0, and varying the oil temperature T. The above first and second aeration sensors 4 have electrode areas S different from each other, and interelectrode distances t different from each other, respectively. In the examples, the electrode area S and the interelectrode distance t in the first aeration sensor 4 are set to respective a value S1 and a value t1, respectively, while in the second aeration sensor 4, the electrode area S and the interelectrode distance t are set to a value S2 and a value t2, respectively. Furthermore, the values of these electrode areas S and interelectrode distances t are set such that the relationships of t1>t2, S1>S2, and S1/t1=S2/t2 hold. Since S1/t1=S2/t2 holds, it is clearly understood from the above equation (1) that the capacitances C of both of the aeration sensors 4 are presumed to be identical so long as the detection is carried out on the same object.

Comparison between the measurement data of the output V in the case of 100% oil and the reference data shown by the dotted line in FIGS. 5A and 5B shows that a thermally-induced drift amount VDT1 in the example employing the first aeration sensor 4 is smaller than a thermally-induced drift amount VDT2 in the example employing the second aeration sensor 4 (VDT1<VDT2).

Figure 6:
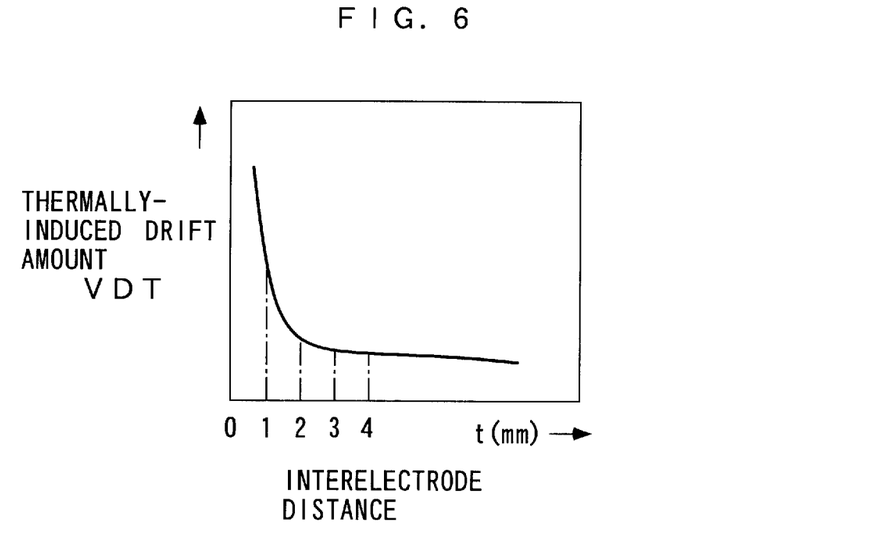
FIG. 6 is a diagram showing the relationship between an interelectrode distance t and a thermally-induced drift amount VDT.

FIG. 6 shows an example of results of measurement of drift amount VDT. In this example, the thermally-induced drift amount VDT is measured when the oil temperature T is equal to the predetermined value T1, assuming that a ratio S/t (ratio of the electrode area S to the interelectrode distance t of the aeration sensor 4) is fixed, and the interelectrode distance t is varied. As shown in the figure, the thermally-induced drift amount VDT sharply decreases as the interelectrode distance t is increased until the interelectrode distance t becomes equal to approximately 2 mm, and starts to gradually decrease when the interelectrode distance t is equal to approximately 2 mm, followed by continuing to gradually decrease thereafter as the interelectrode distance t is further increased. Therefore, it is understood that if the interelectrode distance t is set to a value 2 mm (predetermined value) or larger, it is possible to effectively minimize the thermally-induced drift amount VDT. The interelectrode distance t of the aeration sensor 4 according to the present embodiment is set to 3 mm from this viewpoint, and another viewpoint, described hereinafter. Further, it is demonstrated by experiments that the thermally-induced drift amount VDT is not adversely affected by a variation in the electrode area S although data thereof is not shown here. Therefore, to minimize the thermally-induced drift amount VDT, it is only required to take the interelectrode distance t into account.

Figure 7:
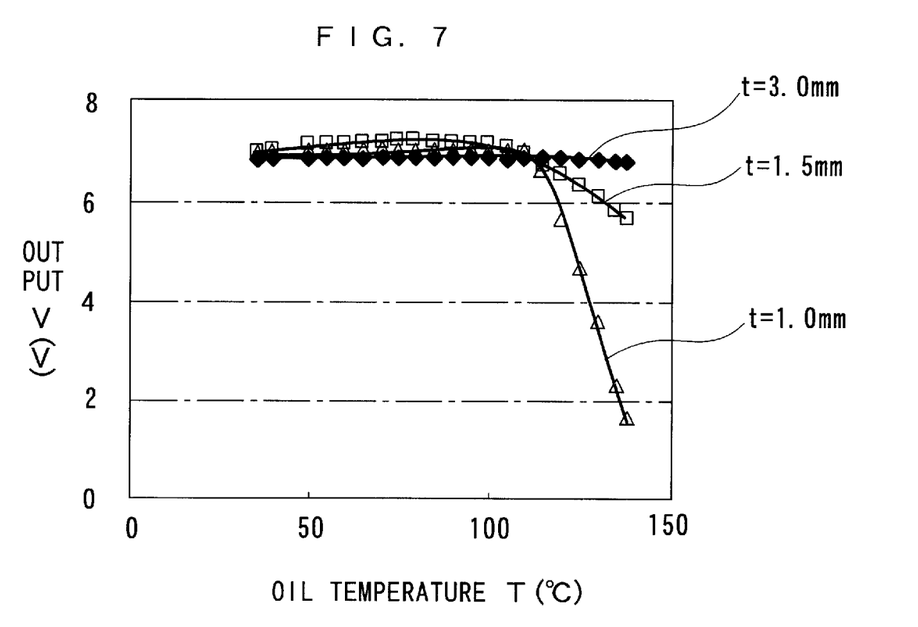
FIG. 7 is a diagram showing results of measurements of the oil temperature T and the output V from the capacitance amplifier, in which the interelectrode distance t is set to three different values.

FIG. 7 shows an example of results of measurement of the output V from the capacitance amplifier 5. In this example, the output V from the capacitance amplifier 5 is measured by setting the interelectrode distance t of the aeration sensor 4 to 1 mm, 1.5 mm, and 3 mm, and varying the oil temperature T (in units of ° C.). From the figure, it is understood that when the oil temperature T is equal to or lower than 100° C., each output V from the capacitance amplifier 5 is stable at or in the vicinity of seven volts which means that the output V is hardly affected by changes in the oil temperature T then. Further, in a region where the oil temperature T is higher than 100° C., the output V in the case of the interelectrode distance t=3 mm, which is employed by the present embodiment, is stable at or in the vicinity of seven volts, and hardly affected by changes in the oil temperature T, whereas in the case of the other interelectrode distances t, the higher the oil temperature T becomes, the more sharply the output V decreases, particularly when the distance t is set to a smaller value, from which it is understood that the output V is more adversely affected as the interelectrode distance of the capacitance amplifier 5 is smaller. As described above, it is understood that the output V from the capacitance amplifier 5 according to the present embodiment is excellent from the viewpoint of detection accuracy, since the output V has a small thermally-induced drift which varies with the oil temperature T, and at the same time varies almost linearly in relation to the oil temperature T.

Figure 8:
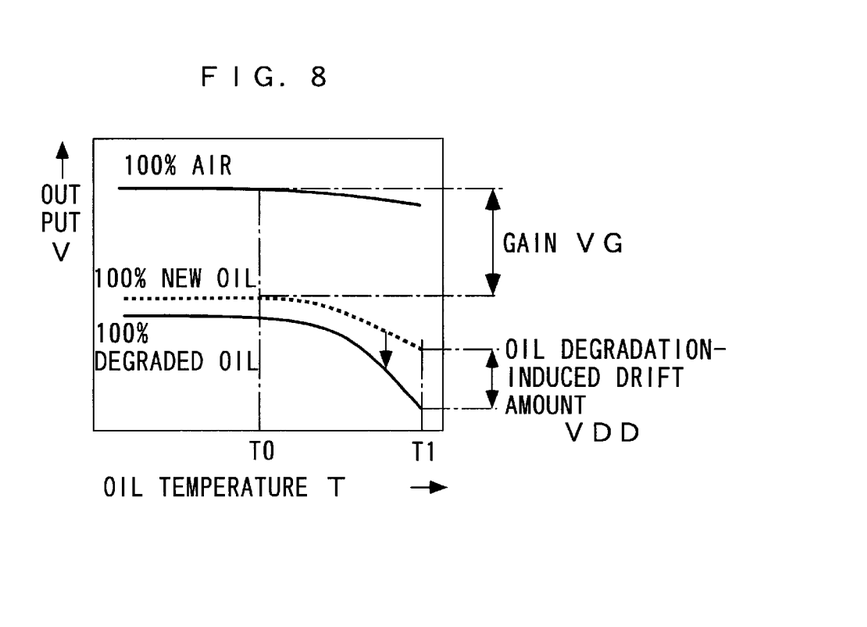
FIG. 8 is a diagram showing the relationship between the oil temperature T and the output V from the capacitance amplifier, which is useful in explaining a drift caused by degradation of oil.

Next, FIG. 8 shows an example of results of measurement of the output V from the capacitance amplifier 5. In this example, the output V is measured by varying oil temperatures T of new oil and degraded oil. In the specification, "degraded oil" is used to mean oil containing oxidized oil, broken polymer, products of abrasion between metals, products of engine combustion, and the like. Comparison between measurement data in the case of 100% new oil shown by a dotted line in the graph and measurement data in the case of 100% degraded oil shown by a solid line in the graph shows that an output V in the case of 100% degraded oil is smaller than an output V in the case of 100% new oil irrespective of the oil temperature T, from which it is understood that a decrease in the value of the capacitance C is caused by a change in the physical properties of the degraded oil due to ingredients thereof. Hereinafter, the absolute value of the difference between an output V in the case of 100% new oil and an output V in the case of 100% degraded oil, both of which are obtained when the oil temperature T is equal to the predetermined value T1, is referred to as the "oil degradation-induced drift amount VDD" (amount of drift).

Figure 9:
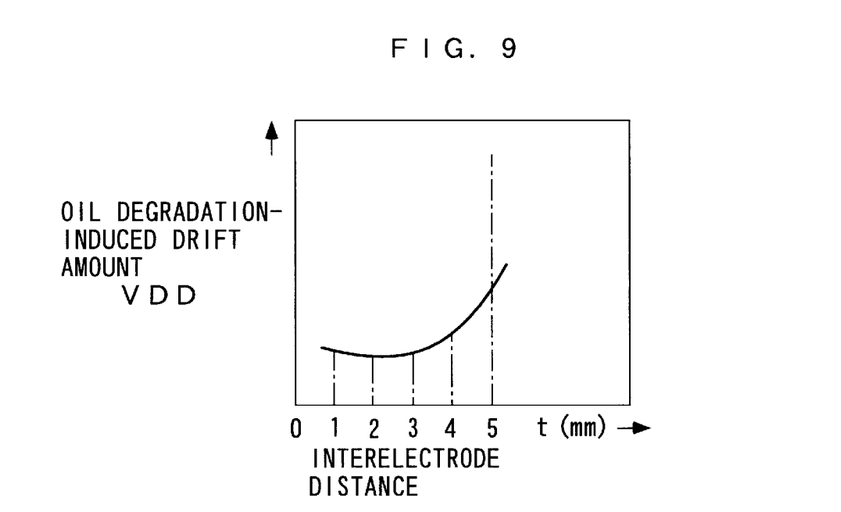
FIG. 9 is a diagram showing the relationship between the interelectrode distance t and an oil degradation-induced drift amount VDD.

FIG. 9 shows an example of results of measurement of the oil degradation-induced drift amount VDD, carried out by varying the interelectrode distance t of the aeration sensor 4. As shown in the figure, the oil degradation-induced drift amount VDD gradually decreases as the interelectrode distance t is increased until the interelectrode distance t becomes close to 3 mm. However, the oil degradation-induced drift amount VDD gradually increases thereafter as the interelectrode distance t is further increased, and in a region of t>5 mm, it sharply increases to assume considerably large values. This shows that it is possible to effectively minimize the oil degradation-induced drift amount VDD if the interelectrode distance t is set to a range between 1 mm and 5 mm (second predetermined value) [$1 \leq t \leq 5$ (mm)].

Therefore, to simultaneously minimize both the increase in the oil degradation-induced drift amount VDD and the increase in the above-mentioned thermally-induced drift amount VDT, it is preferable to set the interelectrode distance t of the aeration sensor 4 to a range of $2 \leq t \leq 5$ (mm), and in this embodiment the interelectrode distance t is set to 3 mm. Further, it is demonstrated by experiments that the oil degradation-induced drift amount VDT is not adversely affected by a change in the electrode area S although data thereof is not shown here. Therefore, to minimize the oil degradation-induced drift amount VDT as well, it is only required to take the interelectrode distance t into account. Further, the electrode area S may be set such that a suitable gain of the capacitance amplifier 5 can be obtained.

Next, the above-mentioned calculation method employed in the thermally-induced drift correction circuit 6 for calculating the air concentration AC (%) of the oil 7 will be described. The thermally-induced drift correction circuit 6 includes a thermally-induced drift correction table shown in FIG. 10. The thermally-induced drift correction table is a look-up table formed by correlating two kinds of measurement data which are obtained by actually measuring the output V from the capacitance amplifier 5 by using the aeration 4 mounted in the oil pan 2 in respective cases of 100% oil and 100% air, to values of the oil temperature T. The two types of measurement data contain not only changes in the output V from the capacitance amplifier 5 caused by changes in the oil temperature T but also changes ascribable to the characteristic of the thermally-induced drift, so that by using these measurement data, the output V from the capacitance amplifier 5 containing thermally-induced drift amount as well can be corrected according to an actual value of the oil temperature T. Therefore, it is possible to calculate the air concentration AC with accuracy, while compensating for the influence of the oil temperature T on the output from the capacitance amplifier 5.

Figure 10:
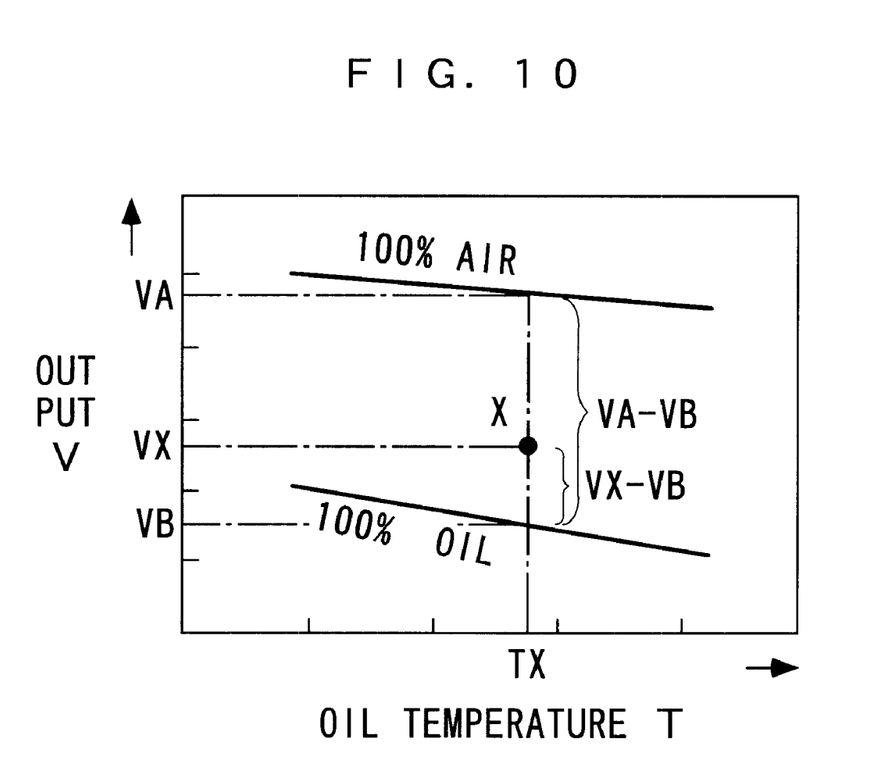
FIG. 10 shows a thermally-induced drift correction table for use in calculating an air concentration AC based on the output V from the capacitance amplifier and the oil temperature T.

More specifically, when the air concentration AC is calculated, the thermally-induced drift correction circuit 6 refers to the thermally-induced drift correction table, and determines values VA, VB of the voltage to be output from the capacitance amplifier 5 in the respective cases of 100% air and 100% oil, which correspond to the value of an actual oil temperature TX detected then by the oil temperature sensor 3. Then, based on the thus determined output values VA, VB and an output VX from the capacitance amplifier 5 at the time point, the thermally-induced drift correction circuit 6 calculates the air concentration AC by the following equation (2). That is, the air concentration AC is calculated by interpolation.

$$AC=[(VX-VB)/(VA-VB)] \times 100(\%) \quad (2)$$

Thus, the thermally-induced drift correction circuit 6 corrects the output V from the capacitance amplifier 5 containing the thermally-induced drift amount, according to the actual oil temperature TX, and calculates the air concentration AC of the oil 7 based on the corrected output V. Further, the circuit 6 outputs a signal indicative of the calculated air concentration AC.

As described above in detail, according to the gas concentration-detecting device 1 of the present embodiment, the capacitance amplifier 5 delivers a signal indicative of a capacitance C between the electrodes 40a, 41a, and the thermally-induced drift correction circuit 6 calculates an air concentration AC of the oil 7 based on the signal. Hence, it is possible to detect the air concentration AC in real time, while coping with changes in the air concentration AC.

Further, as described hereinabove, the thermally-induced drift amount VDT of the output V from the capacitance amplifier 5 has a characteristic that the thermally-induced drift amount VDT is effectively minimized when the interelectrode distance t is equal to or larger than 2 mm. In the present embodiment, since the interelectrode distance t is set to 3 mm, the thermally-induced drift amount VDT of the output V, which is the amount of drift caused by a change in the oil temperature T, can be effectively minimized, and even when the oil temperature T undergoes a drastic change, it is possible to detect the air concentration AC with accuracy.

Further, as described above, the oil degradation-induced drift amount VDD of the output V from the capacitance amplifier 5 is effectively minimized, when the interelectrode distance t is set to a range of $1 \leq t \leq 5$ (mm). Since the interelectrode distance t is set to 3 mm in the present embodiment, the oil degradation-induced drift amount VDD of the output V, which is the amount of drift caused by the degradation of oil can be effectively minimized, and further it is possible to simultaneously minimize both the oil degradation-induced drift amount VDD and the above thermally-induced drift amount VDT. This makes it possible to detect the air concentration AC with higher accuracy.

Further, the thermally-induced drift correction circuit 6 calculates the air concentration AC by correcting the output V of the capacitance amplifier 5 containing the thermally-induced drift amount, according to the actual oil temperature TX. Therefore, it is possible to more effectively reduce adverse influence of a change in the oil temperature T on a signal indicative of a detected air concentration AC, thereby enhancing the accuracy of detection of the air concentration AC.

Figure 11A:
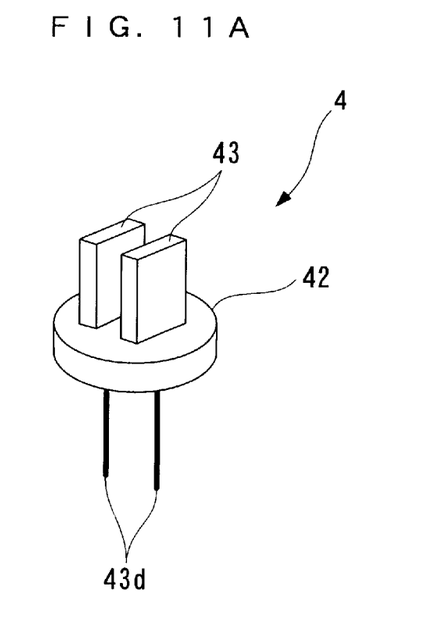
FIG. 11A is a perspective view schematically showing the construction of an aeration sensor of a gas concentration-detecting device according to a second embodiment of the invention.
Figure 11B:
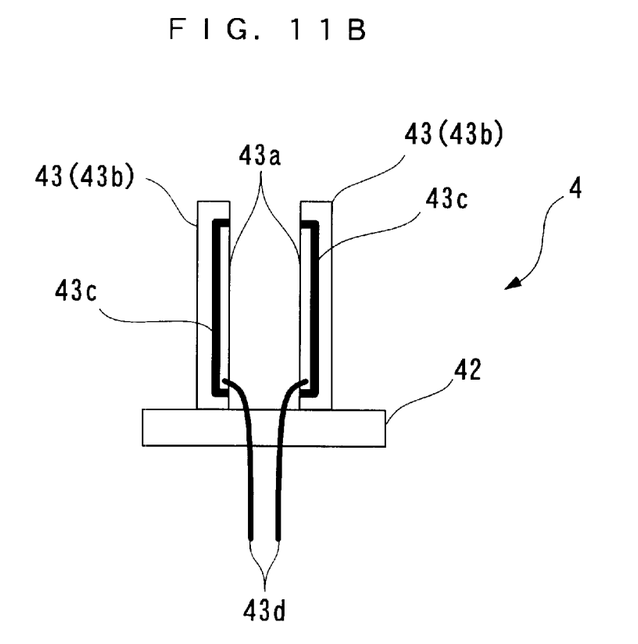
FIG. 11B is a sectional side elevation schematically showing the arrangement of the aeration sensor of the gas concentration-detecting device according to the second embodiment.

Next, a gas concentration-detecting device according to a second embodiment of the invention will be described. The gas concentration-detecting device according to the present embodiment is distinguished from the gas concentration-detecting device 1 according to the first embodiment only in an aeration sensor 4 shown in FIGS. 11A, 11B, and other component parts and elements thereof are configured similarly to the gas concentration-detecting device 1 according to the first embodiment. In the following, the aeration sensor 4 according to the present embodiment is described. As shown in FIGS. 11A and 11B, the aeration sensor 4 includes a disk-shaped base 42, and a pair of electrode portions 43, 43 each in the form of a plate, arranged on the base 42. The base 42 is formed of stainless steel, for instance, and the pair of electrode portions 43, 43 are arranged in a manner opposed to each other at respective locations symmetric with respect to an imaginary center line on one end face of the base 42. Each electrode portion 43 is comprised of an electrode 43a arranged on one surface thereof opposed to the other electrode, a cover 43b covering the other surface opposite to the one surface opposed to the other electrode, an insulating member 43c for electrically insulating the electrode 43a from the cover 43b, and a lead wire 43d connected to the electrode 43a. Each of the two electrodes 43a, 43a is formed e.g. of a coated copper alloy plate (or a stainless plate). The distance between the electrodes 43a, 43a is set to 3 mm which is equal to that between the electrodes according to the first embodiment. Further, the insulating members 43c, 43c are each formed of a synthetic resin, and each cover 43b is formed e.g. of stainless steel. Further, each lead wire 43d has a surface subjected to insulating treatment, and extends vertically through the base 42 from top side to bottom side.

According to the gas concentration-detecting device of the present embodiment incorporating the aeration sensor 4 constructed as above, the same advantageous effects as provided by the gas concentration-detecting device 1 according to the first embodiment can be obtained.

Although in each of the embodiments described above, an example has been described in which the concentration of air in the oil 7 in the oil pan 2 of the lubricating system of an automotive engine is detected by the gas concentration-detecting device 1, this is not limitative, but the concentration of air in oil may be detected in an actuating system of the automotive engine, or further in an oil system of a machine in another industrial field, or in oil itself. Further, the gas of which the concentration is to be detected is not limited to air in oil but concentration of any gas in oil including concentration of carbon dioxide in oil may be detected. Further, although description has been made of an example in which the oil temperature sensor 3 and the aeration sensor 4 are arranged in the oil pan 2, this is not limitative, but the sensors may be arranged in an oil path. Furthermore, the device may be configured such that the output from the capacitance amplifier 5 is corrected not only according to an oil temperature detected by the oil temperature sensor but also according to a hydraulic pressure detected by an oil pressure sensor arranged in the oil path.

The above and other objects, features, and advantages of the invention will become more apparent from the following detailed description taken in conjunction with the accompanying drawings.

What is claimed is:

1. A gas concentration-detecting device for detecting a concentration of gas in oil, comprising:
   a plurality of electrodes for being arranged in said oil such that said electrodes are opposed to each other and spaced from each other by a predetermined distance to form an open space therebetween; and
   a gas concentration detection means for outputting a signal indicative of said concentration of said gas in said oil, said signal being dependent on a capacitance between said electrodes,
   wherein said predetermined distance between said electrodes is set to a value equal to or larger than a predetermined value at which an amount of drift of said signal output from said gas concentration detector dependent on variation in a temperature of said oil starts to gradually decrease as a distance between said electrodes is increased.

2. A gas concentration-detecting device according to claim 1, further including oil temperature detection means for detecting said temperature of said oil, and correction means for correcting said signal output from said gas concentration detection means, according to said temperature of said oil detected by said oil temperature detection means.

3. A gas concentration-detecting device according to claim 1, wherein said predetermined distance between said electrodes is set to a value within a range between said predetermined value and a second predetermined value which is larger than said predetermined value, said range being determined based on a characteristic of said amount of drift of said signal in relation to degradation of said oil.

4. A gas concentration-detecting device according to claim 2, wherein said predetermined distance between said electrodes is set to a value within a range between said predetermined value and a second predetermined value which is larger than said predetermined value, said range being determined based on a characteristic of said amount of drift of said signal in relation to degradation of said oil.

5. A gas concentration-detecting device according to claim 1, wherein said gas concentration detection means comprises a capacitance amplifier which applies a predetermined voltage to said electrodes and detects a voltage generated in response to the application of said predetermined voltage, dependent on said capacitance between said electrodes to output said voltage as said signal.

6. A gas concentration-detecting device according to claim 2, wherein said gas concentration detection means comprises a capacitance amplifier which applies a predetermined voltage to said electrodes and detects a voltage generated in response to the application of said predetermined voltage, dependent on said capacitance between said electrodes to output said voltages as said signal.

7. A gas concentration-detecting device according to claim 6, wherein said correction means includes a lookup table formed by correlating actual measurement values of two kinds of said voltage output from said capacitance amplifier in respective cases of application of said predetermined voltage carried out when said concentration of said gas in said oil is 100% and when said concentration of said gas in said oil is 0% to corresponding values of said temperature of said oil assumed when said application of said predetermined voltage is carried out, and interpolation calculation means for carrying out interpolation calculation by using two values of said actual measurement values of said respective two kinds read from said lookup table according to said temperature of said oil detected by said oil temperature detection means, and an actual value of said voltage output from said capacitance amplifier.

8. A gas concentration-detecting device for detecting a concentration of gas in oil, comprising:
   an outer electrode portion comprising an outer hollow casing and a first electrode fitted in a first end of the outer hollow casing, said outer hollow casing comprising a side wall formed with a slit;
   a first lead wire electrically connected to the outer electrode portion;
   an inner electrode portion comprising an inner hollow casing and a second electrode fitted in a first end of the inner hollow casing, said inner electrode portion mounted in the outer electrode portion, such that the first electrode is opposed to and spaced from the second electrode by a predetermined distance;

a second lead wire electrically connected to the inner electrode portion; and a gas concentration detector for outputting a signal indicative of said concentration of said gas in said oil, said signal being dependent on a capacitance between said electrodes, wherein said slit provides access to a space between the first and second electrodes and said predetermined distance between said electrodes is set to a value equal to or larger than a predetermined value at which an amount of drift of said signal output from said gas concentration detector dependent on variation in a temperature of said oil starts to gradually decrease as a distance between said electrodes is increased.

9. The gas concentration-detecting device of claim 8, wherein the slit has a width equal to the predetermined distance between the electrodes.

10. The gas concentration-detecting device of claim 8, further including an oil temperature sensor for detecting said temperature of said oil, and a drift correction circuit for correcting said signal output from said gas concentration detector, according to said temperature of said oil detected by said oil temperature sensor.

11. The gas concentration-detecting device of claim 8, wherein said predetermined distance between said electrodes is set to a value within a range between said predetermined value and a second predetermined value which is larger than said predetermined value, said range being determined based on a characteristic of said amount of drift of said signal in relation to degradation of said oil.

12. The gas concentration-detecting device of claim 10, wherein said predetermined distance between said electrodes is set to a value within a range between said predetermined value and a second predetermined value which is larger than said predetermined value, said range being determined based on a characteristic of said amount of drift of said signal in relation to degradation of said oil.

13. The gas concentration-detecting device of claim 9, wherein said gas concentration detector comprises a capacitance amplifier which applies a predetermined voltage to said electrodes and detects a voltage generated in response to the application of said predetermined voltage, dependent on said capacitance between said electrodes to output said voltage as said signal.

14. The gas concentration-detecting device of claim 10, wherein said gas concentration detector comprises a capacitance amplifier which applies a predetermined voltage to said electrodes and detects a voltage generated in response to the application of said predetermined voltage, dependent on said capacitance between said electrodes to output said voltages as said signal.

15. The gas concentration-detecting device of claim 14, wherein drift correction circuit includes a lookup table formed by correlating actual measurement values of two kinds of said voltage output from said capacitance amplifier in respective cases of application of said predetermined voltage carried out when said concentration of said gas in said oil is 100% and when said concentration of said gas in said oil is 0% to corresponding values of said temperature of said oil assumed when said application of said predetermined voltage is carried out, and interpolation calculator for carrying out interpolation calculation by using two values of said actual measurement values of said respective two kinds read from said lookup table according to said temperature of said oil detected by said oil temperature detector, and an actual value of said voltage output from said capacitance amplifier.

16. A method of detecting a concentration of gas in oil, comprising the steps of:

providing a gas-concentration detecting device, comprising a plurality of electrodes being opposed to each other and spaced from each other by a predetermined distance and a gas concentration detector for outputting a signal indicative of said concentration of said gas in said oil, said signal being dependent on a capacitance in said oil;

arranging the electrodes in a supply of oil, such that the alectrodes are opposed to each other and spaced from each other by a predetermined distance, wherein said predetermined distance between the electrodes is set to a value equal to or larger than a predetermined value at which an amount of drift of said signal output from said gas concentration detector dependent on vacation in a temperature of said oil starts to gradually decrease as a distance between said electrodes is increased;

measuring a capacitance between the electrodes using the gas-concentration detector; and correlating the capacitance in the oil to the concentration of the gas in the oil.

17. The method of claim 16, further comprising the steps of:

detecting said temperature of said oil, and correcting said signal output from said gas concentration detector according to said temperature of said oil.

18. The method of claim 16, wherein said predetermined distance between said electrodes is set to a value within a range between said predetermined value and a second predetermined value which is larger than said predetermined value, said range being determined based on a characteristic of said amount of drift of said signal in relation to degradation of said oil.

19. The method of claim 19, wherein said predetermined distance between said electrodes is set to a value within a range between said predetermined value and a second predetermined value which is larger than said predetermined value, said range being determined bas ed on a characteristic of said amount of drift of said signal in relation to degradation of said oil.

20. The method of claim 17, wherein said gas concentration detector comprises a capacitance amplifier which applies a predetermined voltage to said electrodes and detect s a voltage generated in response to the application of said predetermined voltage, dependent on said capacitance between said electrodes to output said voltage a s said signal.

21. The method of claim 20, wherein step of correlating comprises correlating actual measurement values of two kinds of said voltage output from the capacitance amplifier in respective cases of application of said predetermined voltage carried out when said concentration of said gas in said oil is 100% and when said concentration of said gas in said oil is 0% to corresponding values of said temperature of said oil assumed when said application of said predetermined voltage is carried out to create a lookup table, and carrying out interpolation calculation by using two values of said actual measurement values of said respective two kinds read from said lookup table according to said temperature of said oil detected by said oil temperature detector, and an actual value of said voltage output from said capacitance amplifier.

22. A gas concentration-detecting device for detecting a concentration of gas in oil, comprising:

a plurality of electrodes for being arranged in said oil such that said electrodes are opposed to each other and spaced from each other by a predetermined distance; and gas concentration detector for outputting a signal indicative of said concentration of said gas in said oil, said signal being dependent on a capacitance between said electrodes, wherein said predetermined distance between said electrodes is between about one millimeter and about five millimeters, such that an amount of drift of said signal output from said gas concentration detector dependent on variation in a temperature of said oil starts to gradually decrease as a distance between said electrodes is increased.

23. A gas concentration-detecting device for detecting a concentration of gas in oil, comprising:

a plurality of electrodes for being arranged in said oil such that said electrodes are opposed to each other and spaced from each other by a predetermined distance to form an open space therebetween; and gas concentration detector for outputting a signal indicative of said concentration of said gas in said oil, said signal being dependent on a capacitance between said electrodes, means for setting the predetermined distance between said electrodes to a value equal to or larger than a predetermined value at which an amount of drift of said signal output from said gas concentration detector dependent on variation in a temperature of said oil starts to gradually decrease as a distance between said electrodes is increased.

24. A gas concentration-detecting device for detecting a concentration of gas in oil, comprising:

a plurality of electrodes for being arranged in said oil such that said electrodes are opposed to each other and spaced from each other by a predetermined distance to form an open space therebetween; and gas concentration detector for outputting a signal indicative of said concentration of said gas in said oil, said signal being dependent on a capacitance between said electrodes, wherein said predetermined distance between said electrodes is set to a value equal to or larger tan a predetermined value at which an amount of drift of said signal output from said gas concentration detector dependent on variation in a temperature of said oil stars to gradually decrease as a distance between said electrodes is increased.

* * * * *